(12) United States Patent
Lee et al.

(10) Patent No.: US 7,298,887 B2
(45) Date of Patent: Nov. 20, 2007

(54) SYSTEM FOR AND METHOD OF ANALYZING SURFACE CONDITION OF PCB USING RGB COLORS

(75) Inventors: Hyo-Soo Lee, Daejeon (KR); Young-Hwan Shin, Daejeon (KR); Chong-Ho Kim, Cheongju-si (KR)

(73) Assignee: Samsung Electro-Mechanics Co., Ltd, Kyunggi-Do (KR)

( * ) Notice: Subject to any disclaimer, the term of this patent is extended or adjusted under 35 U.S.C. 154(b) by 893 days.

(21) Appl. No.: 10/670,096

(22) Filed: Sep. 24, 2003

(65) Prior Publication Data

US 2004/0234119 A1    Nov. 25, 2004

(30) Foreign Application Priority Data

May 19, 2003    (KR) ...................... 10-2003-0031620

(51) Int. Cl.
*G06K 9/00* (2006.01)
(52) U.S. Cl. ...................................................... 382/145
(58) Field of Classification Search ................ 382/145, 382/147, 149
See application file for complete search history.

(56) References Cited

U.S. PATENT DOCUMENTS 4,463,762 A    8/1984  Rubens
6,083,158 A    7/2000  Bearman et al.

FOREIGN PATENT DOCUMENTS

WO    WO 00/11454    *  2/2000

* cited by examiner

*Primary Examiner*—Bhavesh M Mehta
*Assistant Examiner*—Jonathan Schaffer
(74) *Attorney, Agent, or Firm*—Gottlieb, Rackman & Reisman, P.C.

(57) ABSTRACT

A system for and a method of analyzing the surface condition of a PCB using RGB colors are disclosed. The analyzing method includes the steps of feeding a target PCB, to be measured, to an image pick-up position where a pick-up unit is disposed, by a feeding unit, picking up an image of a metal surface of the fed target PCB, extracting pixel data from the picked-up image for the target PCB, performing a mapping operation for RGB signals of the extracted pixel data in accordance with a mapping program, thereby determining relative RGB values, producing cumulative distribution data of the relative RGB values for the target PCB in accordance with an RGB-mapping process, and quantitatively determining the oxidation degree of the target PCB metal surface exhibited with the lapse of time, based on the cumulative distribution data. Since relative values of RGB colors in an image picked up from the metal surface of a PCB can be analyzed, it is possible to rapidly and easily analyze the surface condition of the PCB such as oxidation, contamination, or structural defects of the PCB in a quantitative manner without using an expensive surface analyzer.

9 Claims, 8 Drawing Sheets

SYSTEM FOR AND METHOD OF ANALYZING SURFACE CONDITION OF PCB USING RGB COLORS

BACKGROUND OF THE INVENTION

1. Field of the Invention

The present invention relates to a system for and a method of analyzing the surface condition of a printed circuit board (PCB) using RGB colors and more particularly, a system for and a method of analyzing the surface condition of a PCB using RGB colors, in which the oxidation degree of the PCB is quantitatively measured, based on relative values of RGB signals, in unit pixels of an image obtained by picking up an image of the PCB.

2. Description of the Related Art

PCBs, which are mounted thereon with electronic elements such as semiconductor chips, resistors, and capacitors, serve to electrically connect the mounted electronic elements via conductive wiring patterns of desired shapes or to supply a drive voltage to the electronic elements. Such a PCB includes a board for mounting electronic elements thereon, and wirings of desired patterns for electrically connecting the mounted electronic elements.

The configuration of such a PCB and the procedure for manufacturing the PCB will now be described in detail. A copper clad laminate (CCL) is first prepared by forming a copper film on one surface or both surfaces of a thin substrate made of an insulating material such as epoxy or bakelite resin. In order to increase the bonding force of the copper film to the resin of the substrate, the formation of the copper film is carried out in such a manner that the copper film reacts with the resin of the substrate, thereby penetrating into the resin by a certain depth, for example, about 5 µm.

Thereafter, a shearing process is carried out so as to shear the CCL to have a desired panel size suitable for subsequent processes. The sheared CCL is then subjected to a beveling process, so that it has round corners. Subsequently, the CCL is subjected to a scrubbing process for removing fingerprints or dust on the copper film surface of the CCL or providing roughness to the copper film surface in order to increase the bonding force of a dry film to be laminated on the copper film surface in a subsequent lamination process.

After completion of the scrubbing process, the dry film is formed on the copper film surface. The dry film consists of a film-shaped photoresist adapted to form a desired wiring pattern on a PCB, a Mylar film for providing a certain degree of flexibility, and a cover film.

An artwork film formed with a wiring pattern is then attached to the dry film. Thereafter, the resulting structure is subjected to an exposure process in which ultraviolet rays are irradiated onto the structure so as to cure portions of the photoresist reacting with the ultraviolet rays. At this time, the other portions of the photoresist do not vary. A development process is then carried out using a certain developer, thereby dissolving and, thus, removing uncured portions of the photoresist while leaving the cured photoresist portion to be subsequently used as an etch resist. Thus, an etch mask made of the etch resist is formed on the copper film of the CCL for formation of a desired wiring pattern.

After formation of the etch mask, an etchant is sprayed onto the resulting structure, thereby removing an exposed portion of the copper film corresponding to a region other than a wiring pattern region where the copper film is protected by the etch resist. Accordingly, a desired wiring pattern is formed. After formation of the wiring pattern, the etch resist is completely stripped. Thus, the PCB is completed.

Such a PCB manufacturing method involves repeated processes of lamination, etching and cleaning of copper films, as described above. However, the final product, that is, the PCB, may have a poor surface condition due to contamination sources such as dust or fingerprints left on the copper films, and oxidation or discoloration of the wiring patterns.

In particular, where oxidation occurs at bonding pads of the PCB, made of a metal such as Cu, to be connected to corresponding portions of a semiconductor chip, attachment of balls or wires may not be achieved due to oxides present on the bonding pad surfaces. Although the attachment may be achieved, its bonding strength is considerably low.

Accordingly, it is necessary to measure the degree of an oxidation at the metal surface of a PCB enabling identification of the above mentioned problem. Conventionally, this measurement is achieved with the operator's naked eye or expensive equipment such as a surface analyzer.

However, the method of visually inspecting the surface condition of a PCB by the operator makes it difficult to obtain accurate inspection results because it is greatly influenced by various parameters of the surroundings such as the ability of the operator, surrounding brightness, and time. Furthermore, this method has limited repeatability and reproducibility for the inspection results. For this reason, there is a problem in that it is impossible to obtain quantitative data capable of determining respective qualities of optional PCBs.

On the other hand, where an expensive surface analyzer such as ESCA or Auger is used, it can accurately measure the condition of the metal surface of an optional PCB. However, there are problems in that the surface analyzer increases the manufacturing costs of PCBs due to high installation costs thereof, and cannot be easily applied to products newly developed.

SUMMARY OF THE INVENTION

The present invention has been made in view of the above mentioned problems, and an object of the invention is to provide a system for and a method of analyzing the surface condition of a PCB using RGB colors, in which oxidation, contamination, and structural defects of the PCB are quantitatively measured, based on relative values of RGB signals, in unit pixels of an image obtained by picking up an image of the PCB.

In accordance with one aspect, the present invention provides a system for analyzing a surface condition of a printed circuit board (PCB) using RGB colors, comprising: feeding means for feeding a target PCB, to be measured, to an image pick-up position where pick-up means is disposed; the pick-up means for picking up an image of a metal surface of the target PCB fed by the feeding means, and externally transmitting data of the picked-up image; and signal analyzing means for setting relative RGB values derived through a moisture absorption test carried out for a comparative PCB at intervals of time, extracting pixel data from the picked-up image for the target PCB received from the pick-up means, performing a mapping operation for RGB signals of the extracted pixel data, thereby determining relative RGB values, and comparing the determined relative RGB values with the relative RGB values derived through the moisture absorption test, thereby producing cumulative distribution data of the relative RGB values for the target PCB.

In accordance with another aspect, the present invention provides a method for analyzing a surface condition of a printed circuit board (PCB) using RGB colors, comprising the steps of: setting relative RGB values for PCBs, and storing the set relative RGB values; picking up an image of a target PCB, to be measured, fed by a feeding unit; performing an RGB-mapping process for pixel data extracted from the picked-up image of the target PCB; and producing accumulative distribution data of relative RGB values for the pixel data of the target PCB, thereby quantitatively determining an oxidation degree of the target PCB.

BRIEF DESCRIPTION OF THE DRAWINGS

The above objects, and other features and advantages of the present invention will become more apparent after reading the following detailed description when taken in conjunction with the drawings, in which.

DESCRIPTION OF THE PREFERRED EMBODIMENTS

Now, a system for and a method of analyzing the surface condition of a PCB using RGB signals in accordance with the present invention will be described in detail with reference to the annexed drawings.

First, the configuration and operation of the system for analyzing the surface condition of a PCB using RGB signals in accordance with the present invention will be described in detail with reference to FIG. 1.

Figure 1:
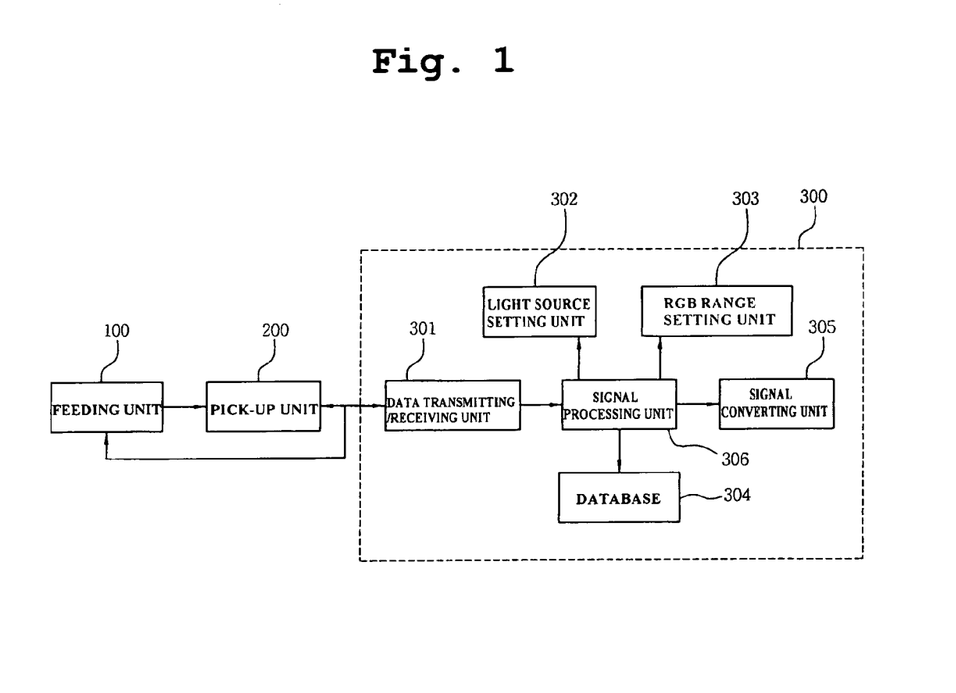
FIG. 1 is a block diagram illustrating a system for analyzing the surface condition of a PCB using RGB colors in accordance with the present invention.

Referring to FIG. 1, a feeding unit 100 is shown which carries a PCB, to be measured, thereon, and feeds the PCB to an image pick-up position where a pick-up unit 200 to be described hereinafter is disposed. The feeding unit 100 includes a conveyor belt connected to a production line for PCBs, and adapted to feed a PCB to the image pick-up position, a sensor installed at a predetermined position on the conveyor belt, and adapted to sense the operating state of the conveyor, a control signal input/output unit for receiving, from a signal analyzing unit 300, a control signal adapted to control the operation of the feeding unit, and a control unit for controlling the whole of the feeding unit.

Although the feeding unit has been described as using the conveyor belt, it is not limited thereto. It may be possible to feed a PCB to the image pick-up position, using a feeding unit having a configuration different from that of the above described feeding unit.

The pick-up unit 200 picks up an image of the metal surface of the PCB fed by the feeding unit 100, divides data of the picked-up image into pixels of a corresponding bitmap, and stores luminance data of the picked-up image data corresponding to each pixel in an internal memory included in the pick-up unit 200.

When a signal requesting inputting of the image data corresponding to the picked-up image of the PCB metal surface is inputted from the signal analyzing unit 300 via a certain communication interface, for example, an RS232C communication interface, the pick-up unit 200 transmits the image data stored in the internal memory to the signal analyzing unit 300.

For the pick-up unit 200 adapted to pick up the image of the PCB metal surface, a digital camera, scanner or charge coupled device (CCD) may be used.

When the signal analyzing unit 300 receives the image data from the pick-up unit 200 via the communication interface, it maps the image data for a selected pixel, using RGB values in predetermined RGB ranges, and measures the degree of oxidation on the associated PCB metal surface, based on the results of the mapping, thereby quantitatively determining whether or not the associated PCB has poor quality. As shown in FIG. 1, the signal analyzing unit 300 includes a data transmitting/receiving unit 301, a light source setting unit 302, an RGB range setting unit 303, a database 304, a signal converting unit 305, and a signal processing unit 306

The data transmitting/receiving unit 301 receives the picked-up image data of the PCB metal surface inputted from the pick-up unit 200 via the communication interface, and then sends the received image data to the signal processing unit 306.

The data transmitting/receiving unit 301 receives various control signals inputted through a data input unit such as a keyboard, to set system operating conditions, for example, a light source setting control signal adapted to set the color temperature and brightness of light, to be irradiated onto the PCB upon picking up an image of the PCB, to certain values, respectively, an RGB range setting control signal adapted to set RGB ranges to be used when RGB-mapping the picked-up image data for a selected pixel, a control signal for controlling the operation of the feeding unit 100, and an image pick-up control signal for controlling the pick-up unit 200. The data transmitting/receiving unit 301 sends the received control signals to the signal processing unit 306.

The data transmitting/receiving unit 301 also receives cumulative distribution data of fractions and relative values of R signals associated with the metal surface of the PCB, and transmits the received cumulative distribution data to a certain output device (not shown) such as a computer monitor or printer via a certain communication interface. The cumulative distribution data is produced by the signal converting unit 305.

The light source setting unit 302 performs a control operation for light emitted from a light source to be used when picking up an image of the PCB metal surface. For example, the light source setting unit 302 controls the color temperature and brightness of the light.

Based on a control signal received from the signal processing unit 306, the RGB range setting unit 303 sets RGB ranges to be applied to an RGB mapping process which will be performed for selected pixel data of the PCB metal surface in accordance with a certain mapping program.

Each of the RGB ranges, that is, R, G, and B ranges, may be set to have level values of 0 to 255 respectively corresponding to different intensity values of a corresponding one of R (red), G (green), and B (blue) signals associated with each pixel of the PCB surface image.

That is, each of the RGB signals, that is, R, G, and B signals, may be represented by 256 intensity levels respectively having level values of 0 to 255. The number of different colors representable in this case is $256^3$ (R×G×B=16,777,216). That is, various colors can be represented by appropriately combining various intensity values of R, G, and B signals. For example, black can be represented by an RGB intensity combination of (0,0,0), bright red (255,0,0), bright green (0,255,0), yellow (255,255,0), cyan (0,255,255), magenta (255,0,255), and white (255,255,255).

The database 304 stores data of R signal fractions (%) and associated relative values measured for the metal surface of the PCB. The R signal fractions are measured at intervals of, for example, 24 hours after performing a moisture absorption test for the metal surface of the PCB under predetermined conditions of, for example, 85° C./60% RH/168 h. The relative value associated with each R signal fraction is calculated by dividing the R signal fraction by an R signal fraction measured at normal temperature for the metal surface of a general PCB not subjected to any moisture absorption test. The following Table 1 shows data of R signal fractions and associated relative values measured at intervals of 24 hours for the metal surface of the PCB after performing a moisture absorption test under the conditions of 85° C./60% RH/168 h.

TABLE 1

Results of RGB Color Analysis of Metal Surface under The Conditions of 85° C./60% RH/168 h

| Conditions | Red Signal Fraction (%) | Relative Value |
|---|---|---|
| 85° C./60% RH/0 h | 22.573 | 1.000 |
| 85° C./60% RH/24 h | 27.094 | 1.200 |
| 85° C./60% RH/48 h | 27.879 | 1.235 |
| 85° C./60% RH/72 h | 29.698 | 1.316 |
| 85° C./60% RH/96 h | 46.071 | 2.041 |
| 85° C./60% RH/120 h | 67.312 | 2.982 |
| 85° C./60% RH/144 h | 67.993 | 3.012 |
| 85° C./60% RH/168 h | 67.994 | 2.012 |

The database 304 also stores data of R signal fractions measured at intervals of time for the metal surface of the PCB after performing a moisture absorption test under severer conditions than those of Table 1, that is, the conditions of 85° C./85% RH/168 h, and associated relative values each measured for the metal surface of the PCB by dividing the associated R signal fraction by an R signal fraction measured at normal temperature for the metal surface of a general PCB not subjected to any moisture absorption test. The data of R signal fractions and associated relative values are shown in the following Table 2.

TABLE 2

Results of RGB Color Analysis of Metal Surface under The Conditions of 85° C./85% RH/168 h

| Condition | Red Signal Fraction (%) | Relative Value | $O_2$ Content (%) |
|---|---|---|---|
| 85° C./85% RH/0 h | 22.573 | 1.000 | 4.021 |
| 85° C./85% RH/24 h | 35.124 | 1.556 | 5.214 |
| 85° C./85% RH/168 h | 73.074 | 3.237 | 16.721 |

The surface condition of the PCB varying with the lapse of time and R signal fraction data representing the variation in PCB surface condition will now be described in detail with reference to Tables 1 and 2.

Referring to Table 1, it can be seen that R signal fractions, and therefore, oxidation degrees, measured at intervals of time for the metal surface of the PCB after performing a moisture absorption test under the conditions of 85° C./60% RH/168 h are distributed in a range from about 22% to about 67%. It can also be seen that relative values respectively associated with the R signal fractions are distributed in a range from about 1.00 to about 3.01.

That is, where oxidation caused by adsorption of moisture is performed for 168 hours, a great increase in R signal fraction is exhibited in a period of time after 72 hours, but before 120 hours. Such a phenomenon is caused by a great increase in the thickness or distribution of oxides formed on the metal surface of the PCB in accordance with oxidation of the metal surface.

After 120 hours, a substantially constant R signal fraction is exhibited. This is because levels of R signals are substantially uniform in accordance with an increase in the scattering degree of reflective visible rays caused by the greatly increased thickness or distribution of oxides on the metal surface of the PCB.

Referring to Table 2, it can be seen that R signal fractions, and therefore, oxidation degrees, measured at intervals of time for the metal surface of the PCB after performing a moisture absorption test under severe conditions of 85° C./85% RH/168 h are distributed in a range from about 22% to about 73%. It can also be seen that relative values respectively associated with the R signal fractions are distributed in a range from about 1.00 to about 3.2. These distributions of R signal fractions and relative values are similar to those of Table 1.

Figure 3:
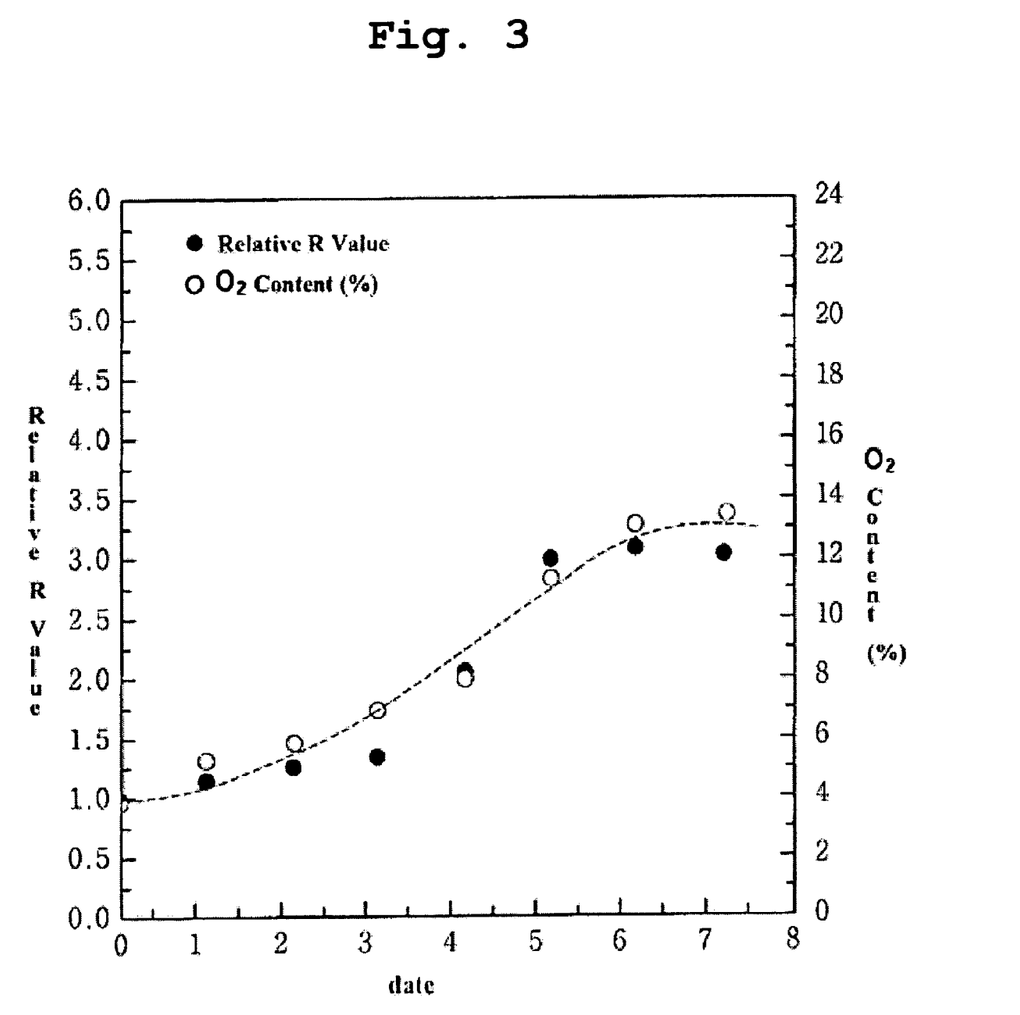
FIG. 3 is a graph depicting the correlation between the $O_2$ content of the PCB metal surface and the relative values of RGB signals varying by the lapse of time.

FIG. 3 shows the correlation between the $O_2$ content of the PCB metal surface at a pixel and the relative values of RGB signals, in particular, the relative value of the R signal, at the pixel. Referring to FIG. 3, it can be seen that the relative value of the R signal and the $O_2$ content (%) varies sharply in a period of time after 72 hours, but before 120 hours.

The signal converting unit 305 converts a relative R signal value, received from the signal processing unit 306 for a selected pixel of the PCB metal surface image, into an electrical signal. In response to a control signal from the signal processing unit 306, the signal converting unit 305 sends cumulative distribution data associated with the PCB metal surface to the data transmitting/receiving unit 301.

The signal processing unit 306 receives various control signals inputted by the operator through a data input unit such as a keyboard, to set system operating conditions, for example, a light source setting control signal adapted to set the color temperature and brightness of light, to be irradiated onto the metal surface of a target PCB, to be measured, upon picking up an image of the PCB, to certain values, respectively, an RGB range setting control signal adapted to set RGB ranges to be used upon RGB-mapping of the picked-up image data for a selected pixel, a control signal for controlling the operation of the feeding unit 100, and an image pick-up control signal for controlling the pick-up unit 200. Based on the received control signals, the signal processing unit 306 performs associated control operations, respectively.

Figure 2:
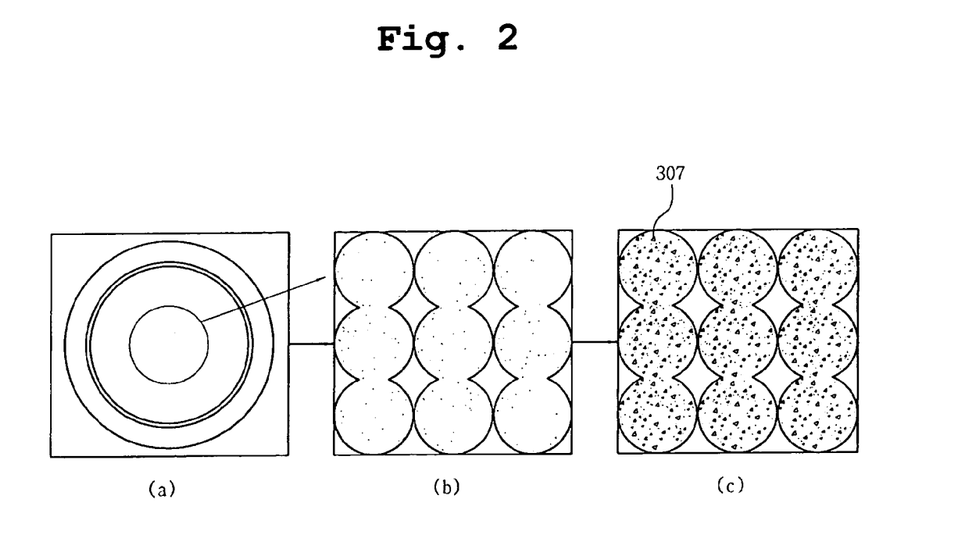
FIG. 2 is a schematic view illustrating pixel data produced by RGB-mapping an image of the metal surface of a PCB by a certain mapping program in accordance with the present invention.

The signal processing unit 306 also receives, from the data transmitting/receiving unit 301, the image data of the PCB metal surface inputted from the pick-up unit 200 to the data transmitting/receiving unit 301 through the communication interface. The signal analyzing unit 300 then runs a mapping program, thereby mapping the image data for a selected pixel, using RGB values in predetermined RGB ranges, as shown in FIG. 2.

Thereafter, the signal processing unit 306 detects RGB signals, in particular, an R signal, from the pixel data of the PCB metal surface image mapped based on the RGB values in the predetermined RGB ranges, and then analyzes the detected R signal associated with the metal surface of the target PCB by comparing the relative value of the R signal with respective relative values of R signals measured at intervals of time for the metal surface of a comparative PCB and stored in the database.

The signal processing unit 306 then sends the relative values of R signals associated with the PCB metal surface to the signal converting unit 305 via the communication interface. Based on the relative values of R signals, the signal converting unit 305 produces cumulative distribution data of RGB signals in the PCB metal surface image.

Based on the cumulative distribution data representing relative values of RGB signals associated with the metal surface of the PCB, the degree of oxidation generated on the PCB is quantitatively determined.

Now, a method for analyzing the surface condition of a PCB, based on RGB colors, using the analyzing system having the above described configuration, will be described in detail with reference to FIGS. 5 to 9.

Figure 5:
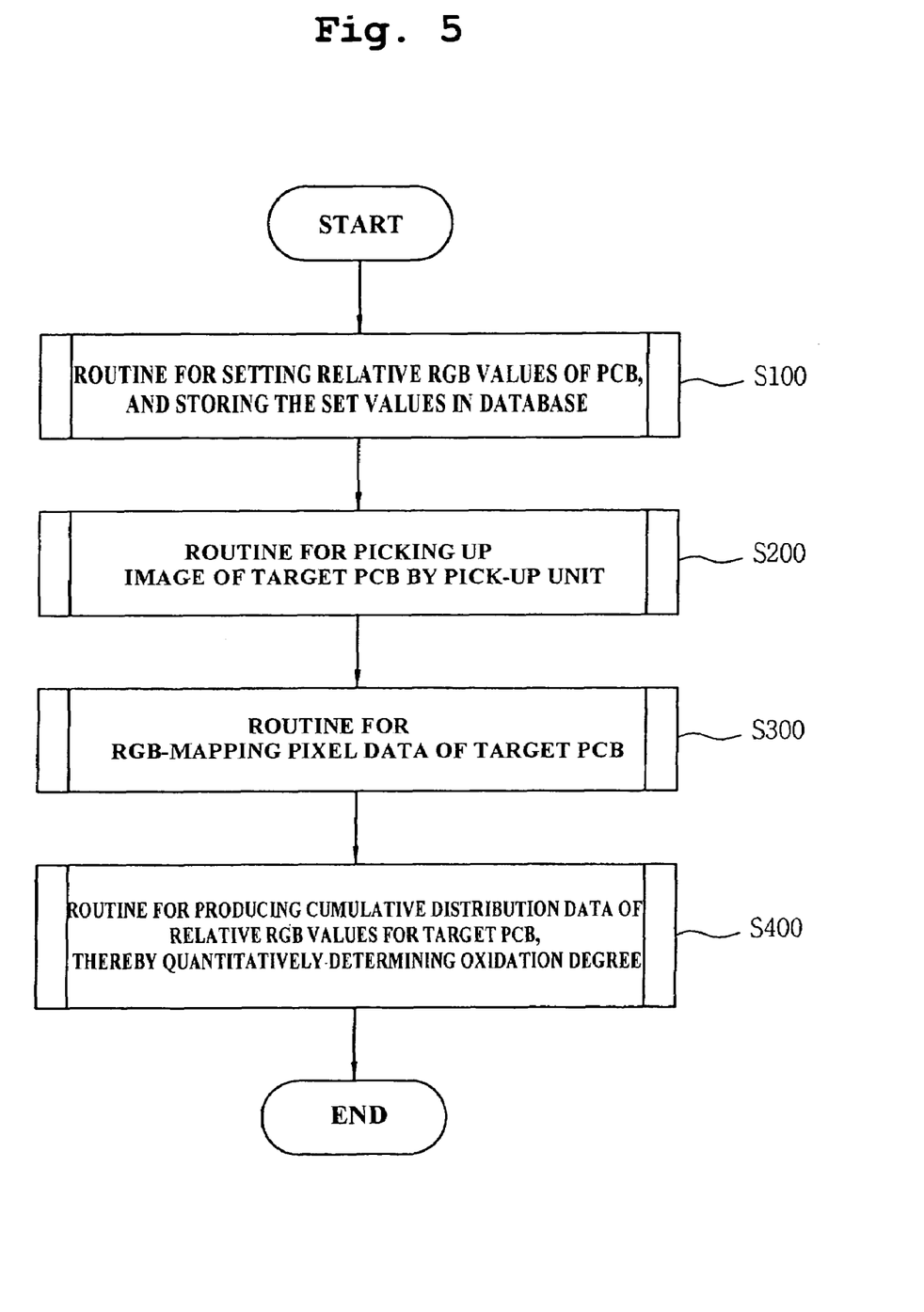
FIG. 5 is a flow chart illustrating a method for analyzing the surface condition of a PCB using RGB colors in accordance with the present invention.

In accordance with the analyzing method, the signal analyzing unit 300 stores relative RGB values measured at intervals of time for the metal surface of a comparative PCB treated under a predetermined condition, as shown in FIG. 5 (S100).

Figure 6:
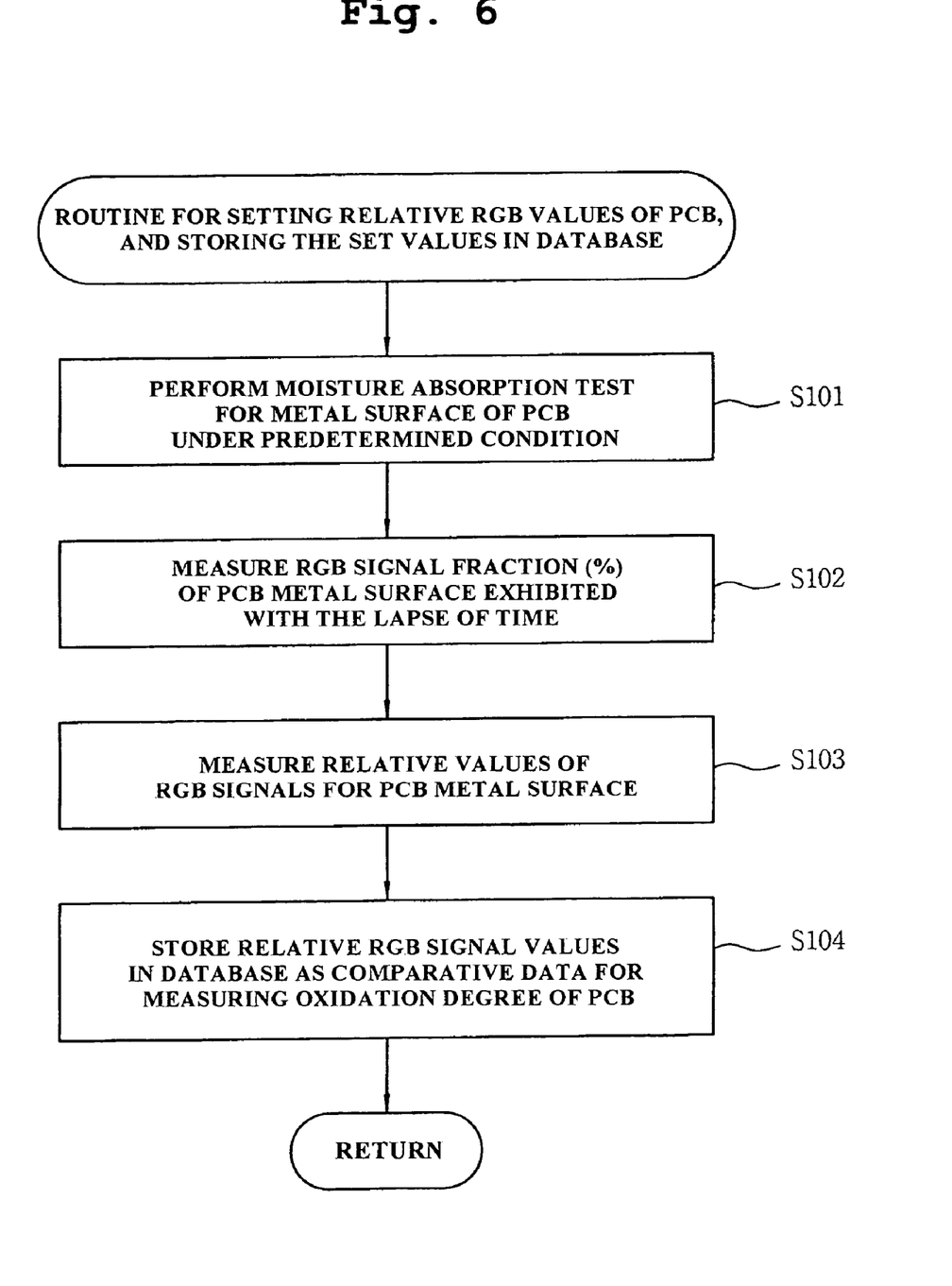
FIG. 6 is a flow chart illustrating a routine for setting relative values associated with a metal surface of the PCB, and storing the set relative values in a database in accordance with the present invention.

This routine will be described in more detail with reference to FIG. 6. A moisture absorption test is carried out for the metal surface of the comparative PCB under certain conditions, for example, conditions of 85° C./60% RH/168 h corresponding to the Level II of JEDEC (Joint Electron Device Engineering Council), or severer conditions of 85° C./85% RH/168 h, as shown in Table 1 or Table 2 (S101).

After execution of the moisture absorption test under the above described conditions, the signal analyzing unit 300 measures, at intervals of time, the R signal fraction for the metal surface of the comparative PCB varying with the lapse of time (S102). The signal analyzing unit 300 then divides each R signal fraction measured at step S102 by a corresponding R signal fraction measured at normal temperature for the metal surface of a general PCB not subjected to any moisture absorption test, thereby deriving a relative RGB value (S103).

The R signal fraction represents the degree of oxidation generated on the metal surface of the PCB. A higher R signal fraction represents an increased oxidation of the PCB metal surface.

Thereafter, the signal analyzing unit 300 stores the derived relative value in the database 304 so that its signal processing unit 306 may use the stored relative value as comparative data when a corresponding R signal value for the metal surface of a target PCB, to be measured, is subsequently inputted to the data transmitting/receiving unit 301 through a certain input unit such as a keyboard or scanner (S104).

After the signal analyzing unit 300 completely stores, in the database 304, the relative values measured at intervals of time for the metal surface of the comparative PCB, the pick-up unit 20 picks up an image of the metal surface of a target PCB fed by the feeding unit 100 for measurement thereof, under the control of the signal analyzing unit 300, as shown in FIG. 5 (S200).

Figure 7:
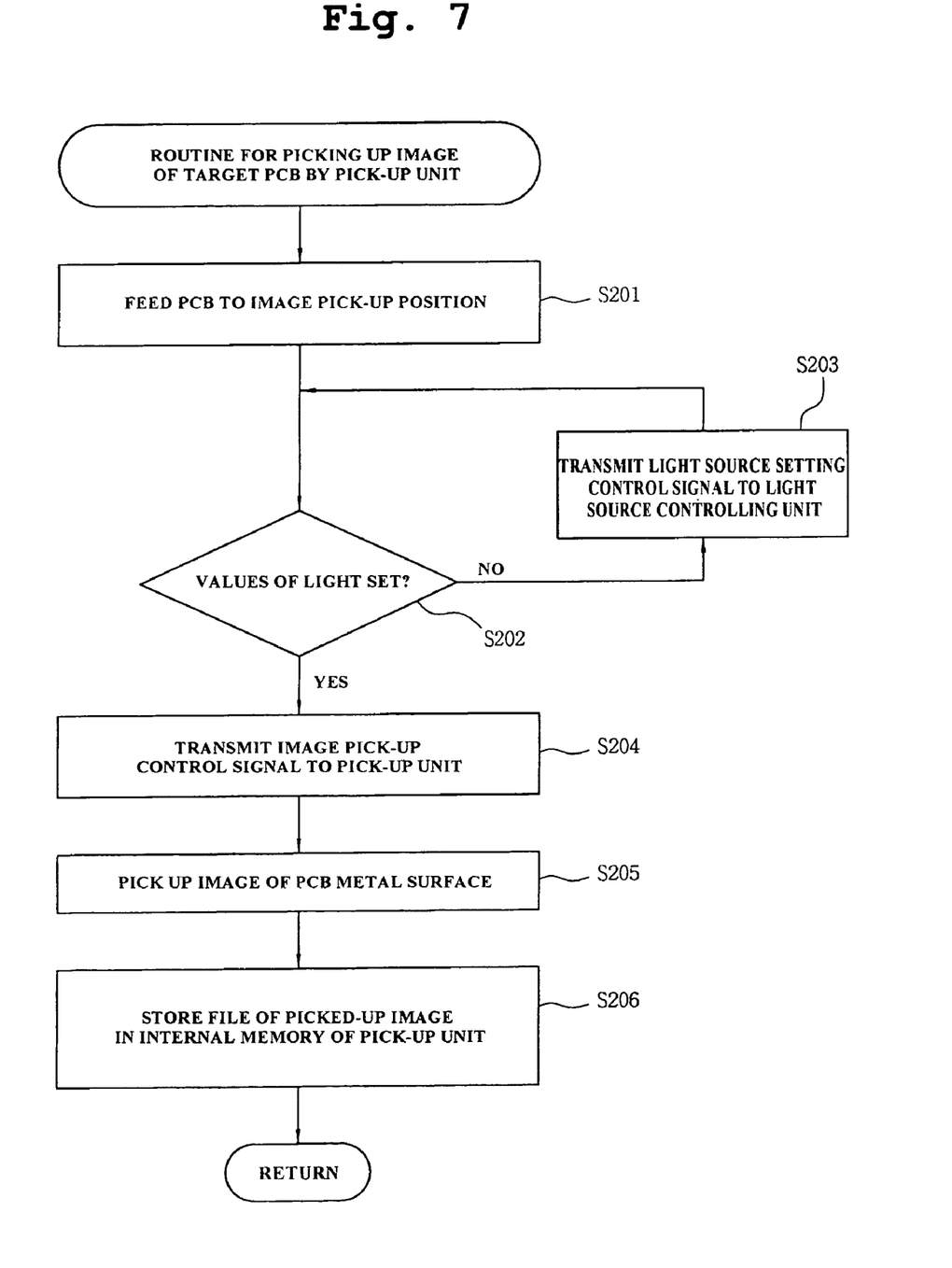
FIG. 7 is a flow chart illustrating a routine for picking up an image of the PCB metal surface by a pick-up unit in accordance with the present invention.

This routine will be described in detail with reference to FIG. 7. When the target PCB reaches the image pick-up position where the pick-up unit 200, which may be a digital camera, scanner, or CCD camera, is disposed, in accordance with the feeding operation of the feeding unit 100 (S201), the signal processing unit 306 of the signal analyzing unit 100 determines whether or not the color temperature and brightness of light to be used upon picking up an image of the PCB are set to predetermined values, respectively (S202).

Where it is determined at step S202 that the color temperature and brightness of light to be used upon picking up an image of the PCB are set to predetermined values, respectively, the signal processing unit 306 of the signal analyzing unit 300 sends a control signal, adapted to control the operation of the pick-up unit 200 for picking up an image of the PCB, to the pick-up unit 200 via the data transmitting/receiving unit 301 (S204).

In response to the image pick-up control signal received from the data transmitting/receiving unit 301 of the signal analyzing unit 300, the pick-up unit 200 picks up an image of the metal surface of the target PCB (S205). The pick-up unit 200 then divides data of the picked-up image into pixels of a corresponding bitmap, and produces respective image data files of the pixels (S206).

After completion of the image pick-up operation for the metal surface of the target PCB by the pick-up unit 200, the signal analyzing unit 300 runs the mapping program, thereby mapping the image data received from the pick-up unit 200 for a selected pixel, as shown in FIG. 5 (S300).

Figure 8:
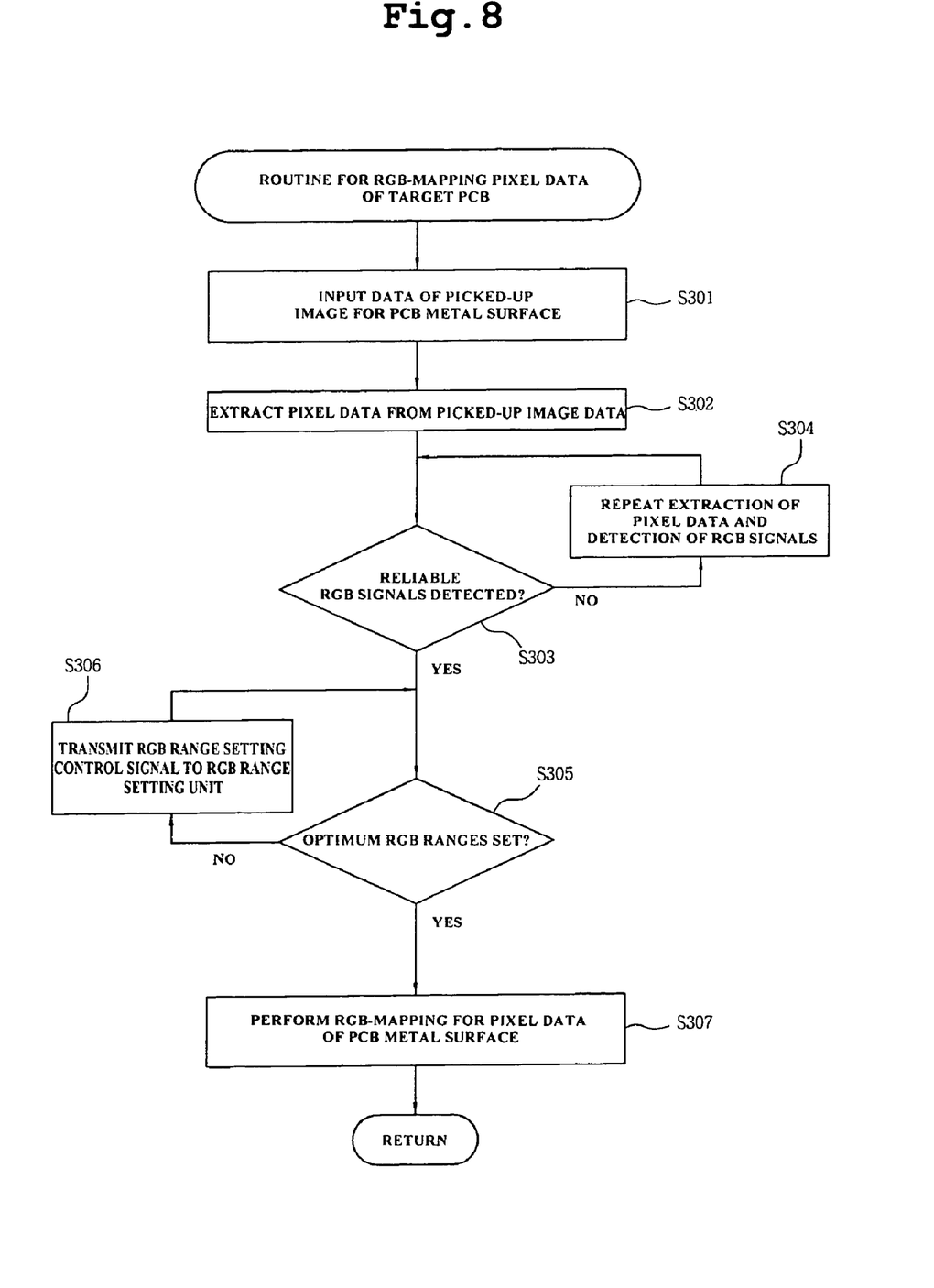
FIG. 8 is a flow chart illustrating a routine for RGB-mapping pixel data extracted from the image of the PCB metal surface in accordance with the present invention.

This routine will be described in detail with reference to FIG. 8. When the signal analyzing unit 300 receives the image data of the PCB metal surface via the communication interface (S301), its signal processing unit 306 runs the mapping program, selects an optional pixel from the bitmap image data, and extracts associated pixel data from the bitmap image data (S302).

Thereafter, the signal processing unit 306 determines whether or not reliable RGB signals are detected from the extracted pixel data of the selected pixel (S303).

When it is determined at step S303 that reliable RGB signals cannot be detected from the extracted pixel data of the selected pixel, the signal processing unit 306 repeats selection of another pixel and extraction of associated pixel data until reliable RGB signals are detected (S304).

On the other hand, when it is determined at step S303 that reliable RGB signals are detected from the extracted pixel data of the selected pixel, the signal processing unit 306 determines whether or not optimum RGB ranges for RGB-mapping of the image data have been set (S305).

Where it is determined at step S305 that the optimum RGB ranges for RGB-mapping of the image data have not been set, the signal processing unit 306 sends a control signal for setting of the optimum RGB ranges to the RGB range setting unit 303, so that the optimum RGB ranges are set in accordance with an operation of the RGB range setting unit 303 (S306).

On the other hand, where it is determined at step S305 that the optimum RGB ranges for RGB-mapping of the image data have been set, the signal processing unit 306 performs an RGB mapping operation for a selected pixel of the image data by running the mapping program, as shown in FIG. 2 (S307).

After RGB-mapping the image data of the PCB metal surface for the selected pixel, the signal analyzing unit 300 produces cumulative distribution data of relative RGB values for the selected pixel of the PCB, and quantitatively determines the degree of oxidation of the PCB, based on the cumulative distribution data (S400).

Figure 9:
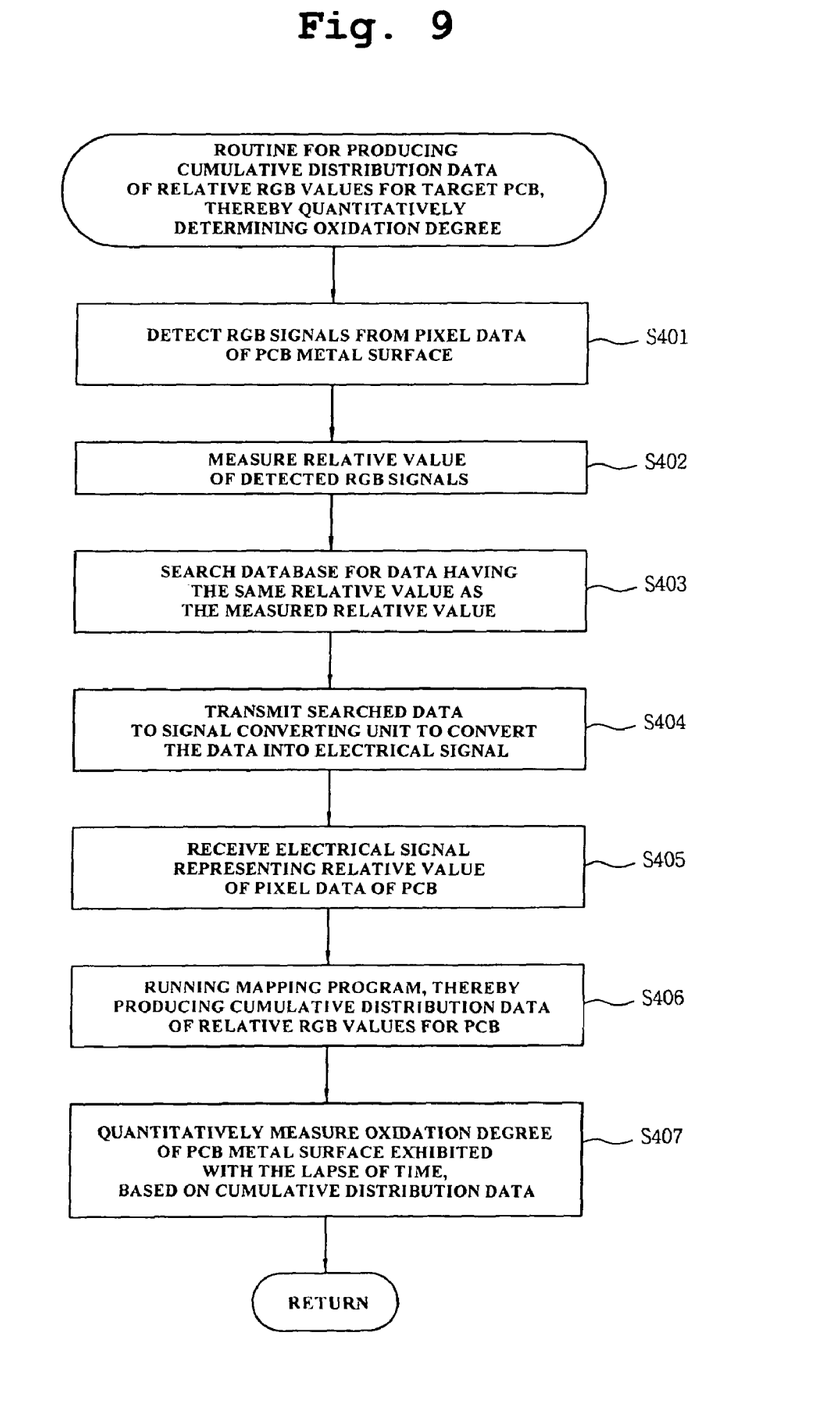
FIG. 9 is a flow chart illustrating a routine for quantitatively determining the oxidation degree of the PCB exhibited with the lapse of time, based on cumulative distribution data of RGB signals in accordance with the present invention.

This routine will be described in detail with reference to FIG. 9. The signal processing unit 306 of the signal analyzing unit 300 detects RGB signals, in particular, an R signal, from a selected pixel of the PCB metal surface image by running the mapping program (S401), and then measures the R signal fraction (%) and relative value of the detected R signal (S402).

Thereafter, the signal processing unit 306 searches data stored in the database 304 for data associated with the same R signal fraction and relative value as the measured R signal fraction and relative value (S403).

The signal processing unit 306 then sends the searched data to the signal converting unit 305 in order to convert the searched data into an electrical signal (S404).

Figure 4:
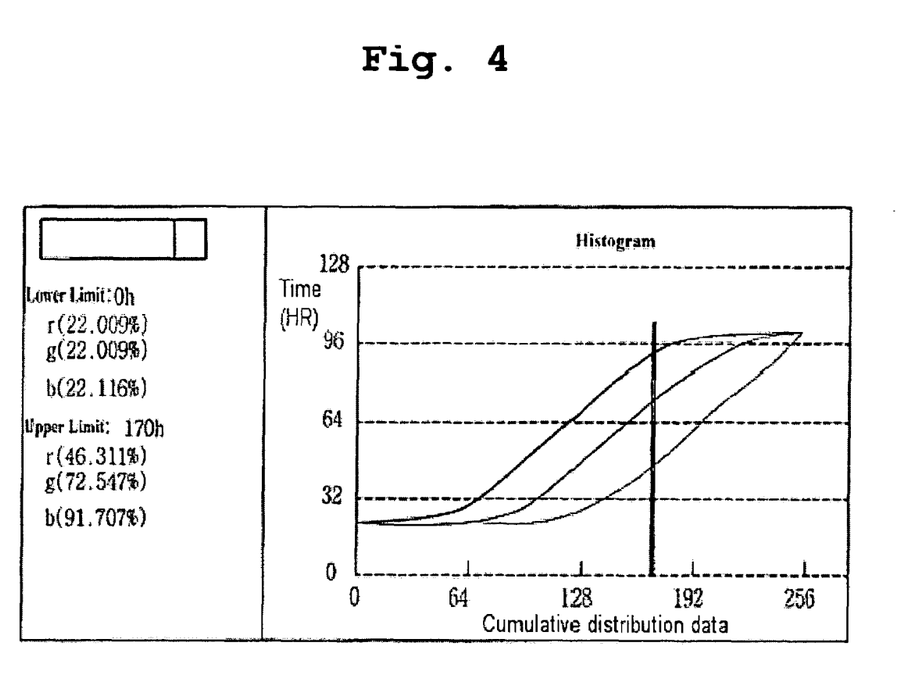
FIG. 4 is a histogram depicting cumulative distribution data of fractions and relative values of RGB signals in pixel data associated with the metal surface of the PCB in accordance with the present invention.

Subsequently, the signal processing unit 306 receives, from the signal converting unit 305, the electrical signal representing the R signal fraction and relative value (S405), and then controls the signal converting unit 305 to produce cumulative distribution data, as shown in FIG. 4 (S406).

Based on the cumulative distribution data of RGB signals produced in association with the metal surface of the PCB in the above described routine, the signal processing unit 306 quantitatively determines the degree of oxidation generated on the metal surface of the target PCB, thereby determining whether or not the target PCB has poor quality (S407).

As apparent from the above description, the present invention provides a system for and a method of analyzing the surface condition of a PCB using RGB colors, which can analyze relative values of RGB colors in an image picked up from the metal surface of a PCB, thereby rapidly and easily analyzing the surface condition of the PCB such as oxidation, contamination, or structural defects of the PCB in a quantitative manner.

In accordance with the present invention, the measure for determining poor quality of PCBs is set in a relative or quantitative manner, based on cumulative distribution data of relative RGB values in the picked-up PCB image. Accordingly, it is possible to considerably reduce the rate of PCBs having poor quality, as compared to the conventional method in which the determination of PCBs having poor quality is achieved with the operator's naked eye.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A system for analyzing a surface condition of a printed circuit board (PCB) using RGB colors, comprising:

feeding means for feeding a target PCB, to be measured, to an image pick-up position where pick-up means is disposed;

the pick-up means for picking up an image of a metal surface of the target PCB fed by the feeding means, and externally transmitting data of the picked-up image; and signal analyzing means for setting relative RGB values derived through a moisture absorption test carried out for a comparative PCB at intervals of time, extracting pixel data from the picked-up image of the target PCB received from the pick-up means, performing a mapping operation for RGB signals of the extracted pixel data, thereby determining relative RGB values, and comparing the determined relative RGB values with the relative RGB values derived through the moisture absorption test, thereby producing cumulative distribution data of the relative RGB values for the target PCB.

2. The system according to claim 1, wherein the pick-up means comprises a digital camera, a scanner, or a charge coupled device.

3. The system according to claim 1, wherein the signal analyzing means comprises:

a data transmitting/receiving unit for receiving the picked-up image data from the pick-up means, and outputting the cumulative distribution data of the relative RGB values for the target PCB produced in accordance with the RGB-mapping operation;

a light source setting unit for setting a color temperature and brightness of light to be used upon picking up the image of the target PCB;

an RGB range setting unit for setting RGB ranges to be applied to a mapping operation to be carried out for the picked-up image of the target PCB in the unit of pixels in accordance with a mapping program;

a database for storing the set relative RGB values representing the oxidation degree of the comparative PCB subjected to the moisture absorption test;

a signal converting unit for converting the relative RGB values derived for the target PCB into an electrical signal; and a signal processing unit for transmitting a light source setting control signal, an RGB range setting control signal, a control signal adapted to control an operation of the feeding means, and an image pick-up control signal to the light source setting unit, the RGB range setting unit, the feeding unit, and the pick-up means, respectively, receiving the picked-up image data inputted through the data transmitting/receiving unit, extracting pixel data from the received picked-up image data for a selected pixel, performing an RGB mapping operation for the extracted pixel data, and determining relative RGB values from the RGB-mapped pixel data, thereby producing cumulative distribution data.

4. The system according to any one of claims 1 to 3, wherein the RGB signals only have R signal components.

5. The system according to claim 1, wherein the feeding means comprises:

a conveyor belt connected to a production line for PCBs, and adapted to feed a PCB from the production line to the image pick-up position;

a sensor installed at a predetermined position on the conveyor belt, and adapted to sense an operating state of the conveyor;

a control signal input/output unit for receiving, from the sensor, a sensing signal representing the sensed operating state of the conveyer, and transmitting the sensing signal to the signal analyzing means, the control signal input/output unit also receiving, from the signal analyzing means, a control signal adapted to control an operation of the feeding means; and a control unit for controlling the operation of the feeding means, based on the control signal.

6. A method for analyzing a surface condition of a printed circuit board (PCB) using RGB colors, comprising the steps of:

(A) setting relative RGB values for PCBs, and storing the set relative RGB values;

(B) picking up an image of a target PCB, to be measured, fed by a feeding unit;

(C) performing an RGB-mapping process for pixel data extracted from the picked-up image of the target PCB; and (D) producing accumulative distribution data of relative RGB values for the pixel data of the target PCB, thereby guantitatively determining an oxidation degree of the target PCB, wherein the step (A) comprises the steps of performing a moisture absorption test for a metal surface of a PCB under a predetermined condition;

measuring values of RGB signals detected from the PCB with the lapse of time after the moisture absorption test;

dividing each of the measured RGB signal values by a corresponding RGB signal value obtained for a PCB not subjected to the moisture absorption test, thereby measuring relative RGB values; and storing the relative RGB values in the database to use the stored relative RGB values as comparative data for measuring the oxidation degree of the target PCB.

7. The method according to claim 6, wherein the step (B) comprises the steps of:

feeding the target PCB to an image pick-up position where a pick-up unit is disposed, in accordance with a feeding operation of the feeding unit;

determining whether or not a color temperature and brightness of light to be irradiated onto the target PCB upon picking up an image of the target PCB are set to predetermined values, respectively;

if the color temperature and brightness of the light are not set to the predetermined values, respectively, sending a control signal, adapted to set the color temperature and brightness of the light to the predetermined values, from a signal analyzing unit to a light source setting unit;

sending an image pick-up control signal, adapted to pick up an image of the PCB, from the signal analyzing unit to the pick-up unit; and picking up an image of a metal surface of the PCB in accordance with the image pick-up control signal, dividing the picked-up image into pixels of a corresponding bitmap, and producing an image data file of the bitmap.

8. The method according to claim 6, wherein the step (C) comprises the steps of:

receiving the picked-up image data of the PCB from the pick-up unit via a communication interface by the signal analyzing unit;

running a mapping program by the signal analyzing unit, thereby extracting pixel data from the picked-up image data of the PCB for a selected pixel;

determining whether or not reliable RGB signals are detected from the pixel data extracted by the signal analyzing unit;

if reliable RGB signals are not detected from the extracted pixel data, repeating the pixel data extraction step and the determination step until reliable RGB signals are detected;

determining whether or not optimum RGB ranges for mapping of the pixel data have been set by the signal analyzing unit;

if the optimum RGB ranges for mapping of the pixel data have not been set, sending a control signal, adapted to set the optimum RGB ranges for the mapping of the pixel data, from the signal analyzing unit to the RGB range setting unit, thereby setting the optimum RGB ranges; and running the mapping program by the signal analyzing unit, thereby RGB-mapping the pixel data of the PCB.

9. The method according to claim 6, wherein the step (D) comprises the steps of:

running a mapping program by the signal analyzing unit, thereby extracting RGB signals from the pixel data of thS:\zoya\Resp,2007\4611-29,doce target PCB;

running the mapping program by the signal analyzing unit, thereby determining a relative RGB value from the extracted RGB signals;

comparing the determined relative RGB value with a corresponding relative RGB value searched for from a database stored with relative RGB values, and converting the determined relative RGB value into an electrical signal; and running the mapping program by the signal analyzing unit, thereby producing cumulative distribution data of relative RGB values of pixel data for the target PCB, and quantitatively determining an oxidation degree of the target PCB exhibited with the lapse of time, based on the cumulative distribution data.

* * * * *